(12) United States Patent
Thornthwaite

(10) Patent No.: US 7,306,919 B1
(45) Date of Patent: Dec. 11, 2007

(54) ANTIGEN-ANTIBODY CANCER RECOGNITION SYSTEM

(76) Inventor: Jerry T. Thornthwaite, 215 Hamlett St., Henderson, TN (US) 38340

( * ) Notice: Subject to any disclaimer, the term of this patent is extended or adjusted under 35 U.S.C. 154(b) by 591 days.

(21) Appl. No.: 10/000,651

(22) Filed: Oct. 31, 2001

(51) Int. Cl.
 G01N 33/00 (2006.01)
 G01N 33/48 (2006.01)
 G01N 33/53 (2006.01)
 G01N 33/563 (2006.01)

(52) U.S. Cl. .................. 435/7.1; 435/7.92; 436/64; 436/513

(58) Field of Classification Search ............... 435/7.1, 435/7.92; 436/64
 See application file for complete search history.

(56) References Cited

U.S. PATENT DOCUMENTS

| | | | |
|---|---|---|---|
| 4,195,017 A | 3/1980 | Bogoch | |
| 4,196,186 A | 4/1980 | Bogoch | |
| 4,298,590 A | 11/1981 | Bogoch | |
| 4,315,851 A | 2/1982 | Yoshikumi et al. | |
| 4,383,985 A | 5/1983 | Bartorelli et al. | |
| 4,389,392 A | 6/1983 | Adachi | |
| 4,401,592 A | 8/1983 | Yoshikumi et al. | |
| 4,444,760 A | 4/1984 | Thomas, Jr. | |
| 4,486,538 A | 12/1984 | Bogoch | |
| 4,565,789 A | 1/1986 | Liotta et al. | |
| 4,571,382 A | 2/1986 | Adachi | |
| 4,624,931 A | 11/1986 | Bogoch | |
| 4,624,932 A | 11/1986 | Bogoch | |
| 4,657,851 A | 4/1987 | Feller et al. | |
| 4,840,915 A | 6/1989 | Bogoch | |
| 4,937,185 A | 6/1990 | Webb et al. | |
| 4,976,957 A | 12/1990 | Bogoch | |
| 4,983,527 A | 1/1991 | Capco et al. | |
| 4,986,256 A | 1/1991 | Cohen et al. | |
| 5,310,653 A | 5/1994 | Hanausek-Walaszek et al. | |
| 5,354,847 A | 10/1994 | Liu et al. | |
| 5,539,094 A * | 7/1996 | Reed et al. .................. 536/23.5 | |
| 5,677,180 A | 10/1997 | Robinson et al. | |
| 5,721,108 A | 2/1998 | Robinson et al. | |
| 5,773,215 A | 6/1998 | Hanauske-Walaszek et al. | |
| 5,866,690 A | 2/1999 | Bogoch | |
| 6,048,685 A | 4/2000 | Alizon et al. | |
| 6,166,176 A | 12/2000 | Radosevich | |
| 6,187,549 B1 | 2/2001 | Schmidt et al. | |
| 6,224,866 B1 * | 5/2001 | Barbera-Guillem ...... 424/130.1 | |
| 6,242,578 B1 | 6/2001 | Bogoch et al. | |
| 6,251,613 B1 | 6/2001 | Kishimoto et al. | |
| 6,261,789 B1 | 7/2001 | Reiter et al. | |

FOREIGN PATENT DOCUMENTS

WO 98/07851 * 2/1998

OTHER PUBLICATIONS

Maeda (Tropical Medicine, 1986, vol. 28, pp. 165-178).*
Jones et al (Surgery, Gynecology and Obstetrics, 1975, vol. 140, pp. 896-898).*
Okada et al (British Journal of Cancer, 1998, vol. 77, pp. 2028-2031).*
Adams et al (Cancer Detection and Prevention, 1994, vol. 18, pp. 65-78).*
Kerr and Thorpe (Immunochemistry, LabFax, 1994, pp. 175-177).*
Fujita et al (British Journal of Cancer, 1999 vol. 81, pp. 769-773).*
Shitara et al, Anticancer Research, 1992, vol. 12, pp. 1121-1129.*
Hembrough et al, Journal of Cell Science, 1995, vol. 108, pp. 1071-1082.*
Ditzel et al, PNAS, 1997, vol. 94, pp. 8110-8115.*
Grubauer et al, (Journal of Investigative Dermatology, 1986, vol. 87, pp. 466-471).*
Ku et al (J Cell Biol. Dec. 28, 1998, vol. 143, pp. 2023-2032).*
Kourtis et al (American Journal of Hepatology, 1994, vol. 46, pp. 283-288).*
Dellagi et al (PNAS, 1982, vol. 79, pp. 446-450).*

* cited by examiner

*Primary Examiner*—Karen A. Canella
(74) *Attorney, Agent, or Firm*—Lanier Ford Shaver & Payne PC; J. Mark Bledsoe

(57) ABSTRACT

A method for the isolation and purification of a cancer recognition (CARE) antigen about 66,000 Dalton molecular weight with a pH between 4.5 and 6.5, and detection of antibodies to this CARE antigen (CARE antibody). The CARE antigen and CARE antibody are cancer markers for a broad range of cancers and can be detected in fluids or tissues of cancer patients with simple ELISA assays. The combined use of these assays for both the CARE antigen and the CARE antibody provide improved sensitivity and selectivity for cancer detection compared to assaying for the antigen or antibody alone. The CARE antigen and antibodies to this antigen have therapeutic usefulness.

11 Claims, 5 Drawing Sheets

Peptide LT104:
```
    1               5              10             15
    AlaValValValLysLysIleGluThrArgAspGylLysLeuValSerGluSerSer
       20         24
    AspValLeuProLys
```

Peptide LT11:
```
    1               5              10             15    17
    CysThrArgAspGylLysLeuValSerGluSerSerAspValLeuProLys
```

Fig. 2

ANTIGEN-ANTIBODY CANCER RECOGNITION SYSTEM

BACKGROUND OF INVENTION

1. Field of Invention

This invention relates generally to the detection of cancer using cancer markers and, more particularly, to a unique antigenic cancer protein and its related specific IgM antibody for the detection of cancers.

2. Technical Background

Cancer is a leading cause of death in men and women throughout the world. However, cancer represents a very heterogeneous group of neoplasms. Because of this heterogeneity, it is difficult to detect or diagnose the presence of cancer in a patient in early stages and the diagnosis of cancer has remained a very difficult task. It is known that cancer occurs because of some abnormality in a gene. A change or abnormality in a gene at its transcriptional level often can lead to the production of proteins which are relatively unique for the cancer cell. These proteins sometimes are useful as markers that are assayable from blood or tissue samples of a patient. A marker is any property which can be used to distinguish cancer from normal tissue and from other disease states. Most markers are antigenic proteins, for example, carcenoembryonic antigen (CEA), Alpha Fetoprotein (AFP), or prostatic specific antigen (PSA). Others include CA 125, CA 15-3, and CA 19-9. These antigens are usually detected by using the antibody which is relatively specific for these antigenic markers. The assays using these markers have not to date been markedly predictive of the presence of cancer in patients. The sensitivity and specificity of these antigenic marker assays has been relatively low. For any screening test to have sufficient utility in a clinical setting, it must display adequate sensitivity and specificity. Sensitivity is defined as the probability that a test will be positive given that the patient has the disease. Specificity of the test refers to the probability that the test will be negative provided that the disease is absent. In addition, many of the commercially available tests are only applicable to a narrow range of cancer types and these tests suffer not only from the disadvantage that other types of cancer may be missed, but also from the disadvantage that a narrow applicability of the tests requires running multiple tests on a single patient. The ideal marker is one that is specific and universal, resulting from the expression of the unique gene product in all kinds of transformed cancer cells.

Although, most cancer markers are antigenic proteins, some cancer markers are antibodies. For example, an anti-GAD2 antibody has been used in conjunction with the GAD2 antigenic protein to measure GAD2 antibody which occurs in hepatic cancer. The method of detecting the presence of autoantibodies on the fetalphosphal protein in patients having cancer is also known. U.S. Pat. No. 4,840,915 issued to Bogosh in 1989 describes the use of a tumor antigen called malignin to measure antibody as a cancer marker. In U.S. Pat. No. 5,866,690 Bogosh disclosed that malignin antibodies were IgM antibodies. In 2000, Thornthwaite published the results of a clinical study using the malignin antigen to measure antimalignin antibodies as cancer markers in breast cancer patients. Other cancer antigen markers were used for comparison in this clinical study which demonstrated that measurement of the malignin antibody was more sensitive (97%) in detecting breast cancer than the measurement of the antigens, CEA 0%, CA 15-3 (10%), CA 19-5 (5%), or CA 125 (16%).

Antibodies are immunoglobulins which combine antigens specifically. The use of antibodies and immunoassays for the detection of minute amounts of substances in physiological fluids is well known in the art. The assay basically depends on the binding interaction between an antigen and an antibody therefor. In the great majority of systems described in the prior art, the antibody is usually immunoglobulin G (IgG). Both polyclonal and monoclonal IgG's have been used. IgM is a well known 19S immunoglobulin which comprises about 7% of the immunoglobulins found in man. IgM antibodies are the earliest antibodies generated in the immune response. Although IgM antibodies tend to be very effective, especially in combating bacterial infections, they have a relatively short in vivo half life of about 5 days. The use of IgM antibodies has received relatively less attention in the immunoassay art in the diagnosis of cancer. IgM antibodies tend to aggregate and are relatively difficult to stabilize, especially in the purified form. They are very sensitive to reducing agents, they self-aggregate and precipitate out of solution, and have been found to bind in a nonspecific manner. Also, they are considered to have substantially less binding affinities for antigens than IgG antibodies. For these reasons, IgMs have not been utilized in immunoassays except in rare instances. One would not expect an IgM antibody to be useful to measure the presence of an antigen cancer marker.

The present invention provides new cancer markers utilizing an IgM antibody that is highly specific for a new cancer related antigen that appears to be common in a wide range of cancers. This cancer recognition system of the present invention provides a means for the detection of cancer in a broad range of cancers with relatively high selectivity and specificity. Furthermore, this novel antigen and its related antibody may also have utility in the treatment of cancers.

SUMMARY OF INVENTION

The present invention provides for the isolation and purification of a cancer recognition protein obtained from cancer cells using iso-electric focusing, size exclusion chromatography of fractions within a pH range of 5.5 to 7.5, and concentration centrifugation. The cancer recognition (CARE) protein (antigen) material so isolated has molecular weights ranging from between 2,000 to 70,000 Daltons, a pKa ranging from 4.5–6.5, and an IgM binding region. An antibody to the CARE antigen can be produced by inoculating chickens with the CARE antigen and extracting IgY antibody from the egg yolks produced by the inoculated chickens. An ELISA test incorporating the CARE antigen can be used to measure antibody to the CARE antigen (CARE antibody) in the tissues or fluids of patients for a large variety of cancers. Antibodies to the CARE antigen can also be produced in rabbits and mice. Using this assay, patients with a history of cancer were shown to have 7 times higher serum CARE antibody levels than normal subjects. Likewise, an ELISA test incorporating the IgY antibody to the CARE antigen can be used to measure the CARE antigen in tissues or fluids of patients for a large variety of cancers. Using this assay, patients with various cancers were shown to have 2.6 times higher serum CARE antigen levels than normal subjects. This increased CARE antigen level was associated with an 11 times higher CARE antibody level. The present invention further provides a combination ELISA CARE antigen/antibody test to measure both cancer markers to further increase the sensitivity and selectivity of cancer detection.

An advantage of the present invention is that it provides a method for detecting disease utilizing an assay to detect an antigenic substance relatively specific for that disease and to detect an IgM antibody specific for that antigenic substance.

Another advantage of the present invention is that it provides a method for detecting cancer utilizing an assay to detect an antigenic substance relatively specific for that cancer and an assay to detect an antibody specific for that antigenic substance.

Another advantage of the present invention is that it provides an antigenic protein or a cancer recognition antigen found in a large variety of cancers which is useful in the detection of cancer as a cancer marker.

Another advantage of the present invention is that it provides a specific IgM antibody to the cancer recognition antigen which is useful in the detection of cancer as a cancer marker.

Another advantage of the present invention is that it provides a simple ELISA assay for the cancer recognition CARE antigen for the detection of cancer.

Another advantage of the present invention is that it provides a simple ELISA assay for the antibody to the CARE antigen (CARE antibody) for the detection of cancer.

Another advantage of the present invention is that it provides a simple method for the isolation and purification of the CARE antigen.

Another advantage of the present invention is that it provides a simple method for the production of an antibody to the CARE antigen (CARE antibody).

Another advantage of the present invention is that it provides a therapeutic treatment of cancer using the CARE antigen as a vaccine.

Another advantage of the present invention is that it provides a therapeutic treatment of cancer using an IgY antibody to the anti-CARE antigen to induce an immune response against cancer cells.

Another advantage of the present invention is that it provides cancer marker assays for the detection of cancer which are compact, simple, easy to use, rapid, and inexpensive.

Another advantage of the present invention is that it provides an antigenic protein specific for a wide range of cancers which can be isolated and purified from any source of cancer or tumor cells.

Another advantage of the present invention is that it provides cancer marker assays for the detection of cancer which are safe and meet all regulatory standards including those of the FDA, the EPA, and OSHA.

Another advantage of the present invention is that it provides a method for producing CARE antibodies from any biological source capable of producing antibodies both in vivo and in vitro.

BRIEF DESCRIPTION OF THE DRAWINGS

FIG. 2 shows the amino acid sequence of two fragments of the CARE antigen which bind to CARE antibody (SEQ ID NOs: 1 & 2).

DETAILED DESCRIPTION OF THE PREFERRED EMBODIMENTS

While the following description details the preferred embodiments of the present invention, it is to be understood that the invention is not limited in its application to the details of construction and arrangement of the parts illustrated in the accompanying drawings, since the invention is capable of other embodiments and of being practiced in various ways.

1. Isolation and Purification of the CARE Antigen

Figure 1:
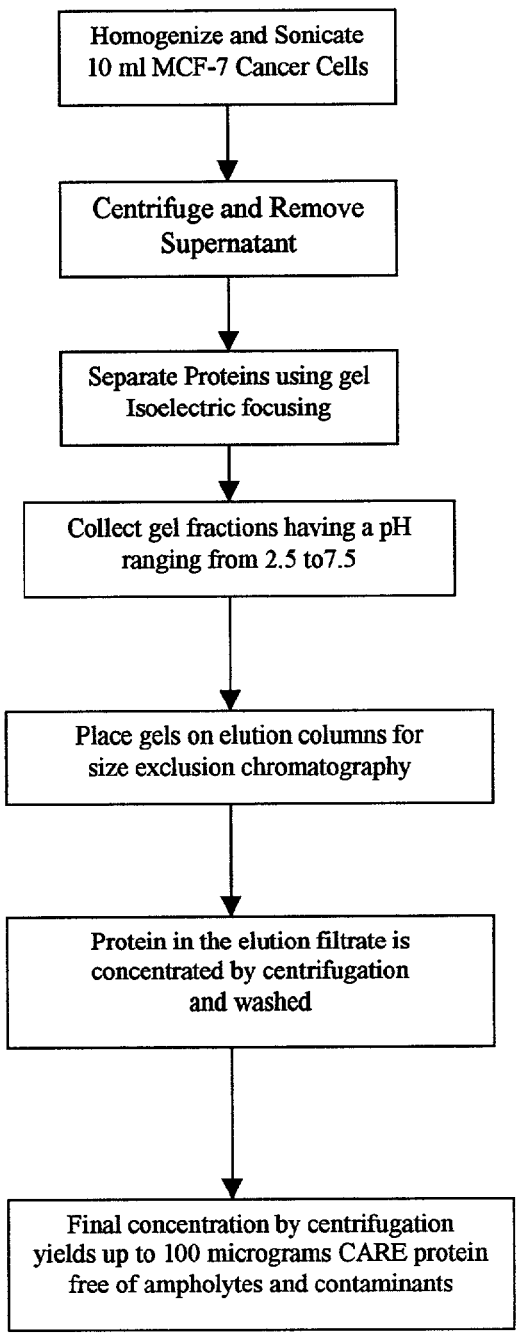
FIG. 1 shows the method for isolation and purification of the CARE antigenic protein from cancer tissue.

The method for the isolation and purification of the CARE antigen is shown in FIG. 1. Ten ml of commercially available MCF-7 human breast cancer cells were combined with 10 ml of 0.2% triton X-100 in water and homogenized on ice for 30 seconds. Homogenate was then sonicated on ice for 2 one minute intervals separated by a one minute rest period. Cell debris was removed by centrifugation at 2,135×G and then the supernatant was removed and recentrifuged at 10,000×G for 10 minutes Final supernatant was incorporated into a preparative granulated gel for isoelectric focusing and separated under 8 W constant power overnight at 10° C. Power was increased to 20 W for the final hour of separation. Fractions were collected and combined with water. Those fractions having a pH in the range of 3.5 to 7.5 were transferred to elution columns for size exclusion chromatography and the liquid portion was allowed to drain by gravity. The filtrates were transferred to 10,000 nominal molecular weight micron concentrator tubes and centrifuged at 14,000×G for 30 minutes in a fixed angle centrifuge. The aqueous portion above the concentrated material was removed and the concentrated material was then diluted in water and recentrifuged. The final protein concentrate was collected, and it provided 100 micrograms of CARE antigen protein. The drained gel portions can be washed by resuspension in water and in turn drained again using the filtrates as described above to increase the yield of CARE antigenic protein. To identify the proteins comprising the antigenic substance of the present invention, a portion of the final concentrate was applied to a 10–20% gradient SDS-PAGE gel under denaturing conditions. The gel was stained with Coomassie R-250 and then destained until the bands were adequately visible. The appearance of the Dalton bands in the fractions which range in pH from 3.5 to 7.5 are the preferred antigenic cancer marker proteins of the present invention. These proteins range in Daltons from 2,000 to 70,000. The pKa of these proteins ranges between 4.0–8.0, preferably 4.5–6.5. These proteins have an IgM binding region. The preferred protein comprising these CARE antigens of the present invention occurs in fractions that have a pH of 5.5 and a pKa ranging between 4.5–6.5. This is about a 66,000 Dalton protein that represents the preferred embodiment of the present invention. The 66,000 Dalton band was subjected to fast protein liquid chromatography for performing amino acid sequence analysis.

The CARE antigen was analyzed for amino acid sequences or fragments that bind to the CARE antibody. Two polypeptides were discovered which represent the binding site of the CARE antigen. The amino acid sequences of those two polypeptides are shown in FIG. 2. The following amino acid sequence:

Thr Arg Asp Gyl Lys Leu Val Ser Glu Ser Ser Asp Val Leu Pro Lys
1  5  10 15 is common to both polypeptides. Binding studies of the CARE antibody to these polypeptides were performed.

Binding of the CARE antibody to the isolated polypeptides correlated well (correlation coefficient=0.88) with CARE antibody biding to the whole tumor homogenate.

Other methods may be used for the purification and detection of the CARE antigen of the present invention, including but not limited to, thin layer chromatography, ion exchange chromatography, affinity chromatography, ultra filtration, ultra centrifugation, formation of antigen/antibody complexes, or a combination thereof. The use of an antigen/antibody complex in the detection or purification of the CARE protein may include developing a first antibody to the CARE antigenic protein and then developing a second antibody to the first antibody. The first antibody may be found in human blood and/or any human fluid and/or cells, including tissues against the CARE protein antigen wherein the CARE protein antigen is bound to a surface. Competitive binding assays between the patient's antibody and an antibody from any source may be used wherein the CARE antigenic protein antibody can be bound to the inside of a multiwell plate. The antibodies and the CARE antigenic protein may be fragmented. The fragment of the CARE antigenic protein may be an amino acid sequence that is the active binding sight for antibody. The CARE antigenic protein may be bound to a dipstick and antigen/antibody complexes can be precipitated with metal complexes, a gold bound antibody or a dye bound antibody. The antigen/antibody complex can be detected by reflection, color, fluorescence, chemiluminescence, conductivity, electromagnetic frequency vibration, and light scatter differences in the antigen/antibody complex.

The antigen/antibody complexes can also be detected in a western blot assay. This assay was performed, for example, as follows. A 15 pl aliquot of the CARE Antigen Protein was subjected to SDS-PAGE, and then transferred to Costar Bio-blot nitrocellulose using an LKB semi-dry transfer apparatus. The membrane was blocked with 5% dry milk in PBS for one hour. The blot was then incubated overnight at room temperature in one of the three solutions. In the first solution, the blot was incubated with a 1:100 dilution of primary patient serum (diluted in PBS containing 3% BSA). In the second solution the blot was incubated with a 1:100 dilution of our negative serum. In the third solution the blot was incubated in dilution buffer alone (no primary serum). After incubation the blots were rinsed exhaustively with PBS, and then one of two sample lanes on each blot were cut apart and incubated in either anti-human IgG or anti-human IgM, both of which were conjugated to alkaline phosphatase. These secondary antisera were diluted 1:10,000 in antibody buffer. The blots were then incubated for one hour at room temperature, washed extensively, and then developed with substrate (BCIP) for alkaline phosphatase.

Figure 3:
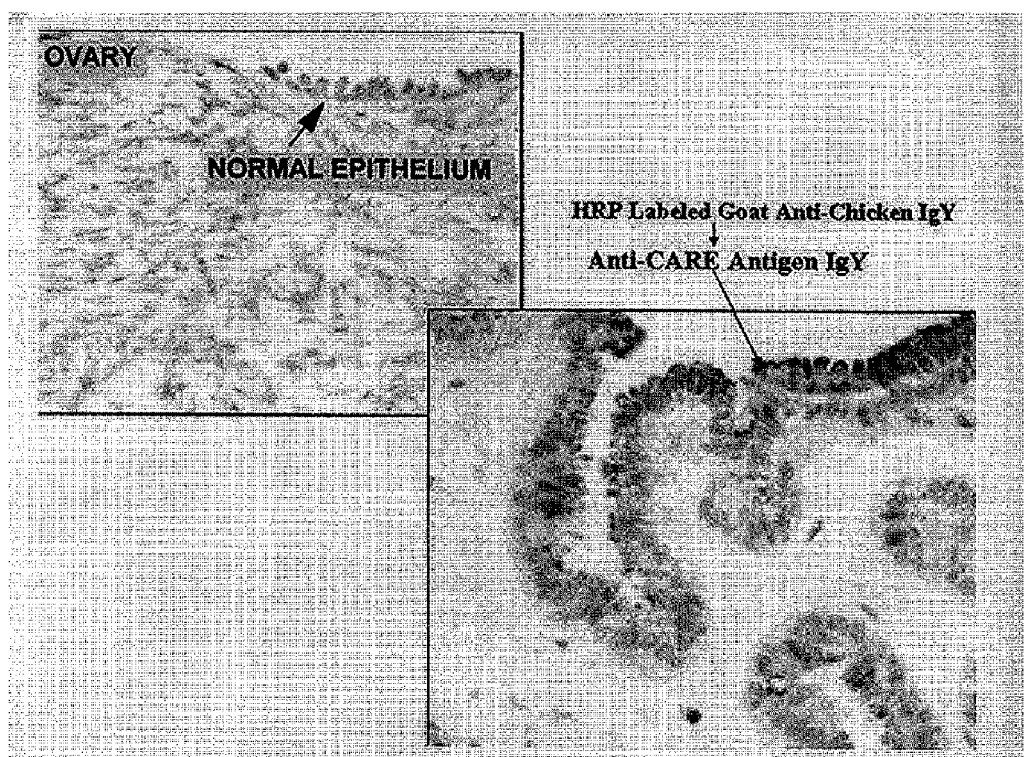
FIG. 3 shows the ELISA method for the detection of the CARE antibody in serum.

In order to demonstrate the presence of the CARE antigen on cancer cells, a study was performed in patients having ovarian carcinoma. Cancerous ovarian tissue was removed from these patients and analyzed for the presence of the CARE antigen using histologic methods. The tissues were exposed to IgY, a purified IgG from chickens immunized with the CARE whole antigen preparation. This IgY antibody binds specifically to the CARE antigen in tissues. A secondary antibody to the chicken IgY, derived from goat and having horseradish peroxidase (HRP) attached to it, was then added. The HRP was then reacted with a dye which stains brown in the presence of the HRP. The brain stain reflects the region where the CARE antigen resides. Normal ovarian tissue did not stain while staining was consistently present in cancerous tissue, as shown in FIG. 3.

2. CARE Antibody ELISA Test.

Figure 4:
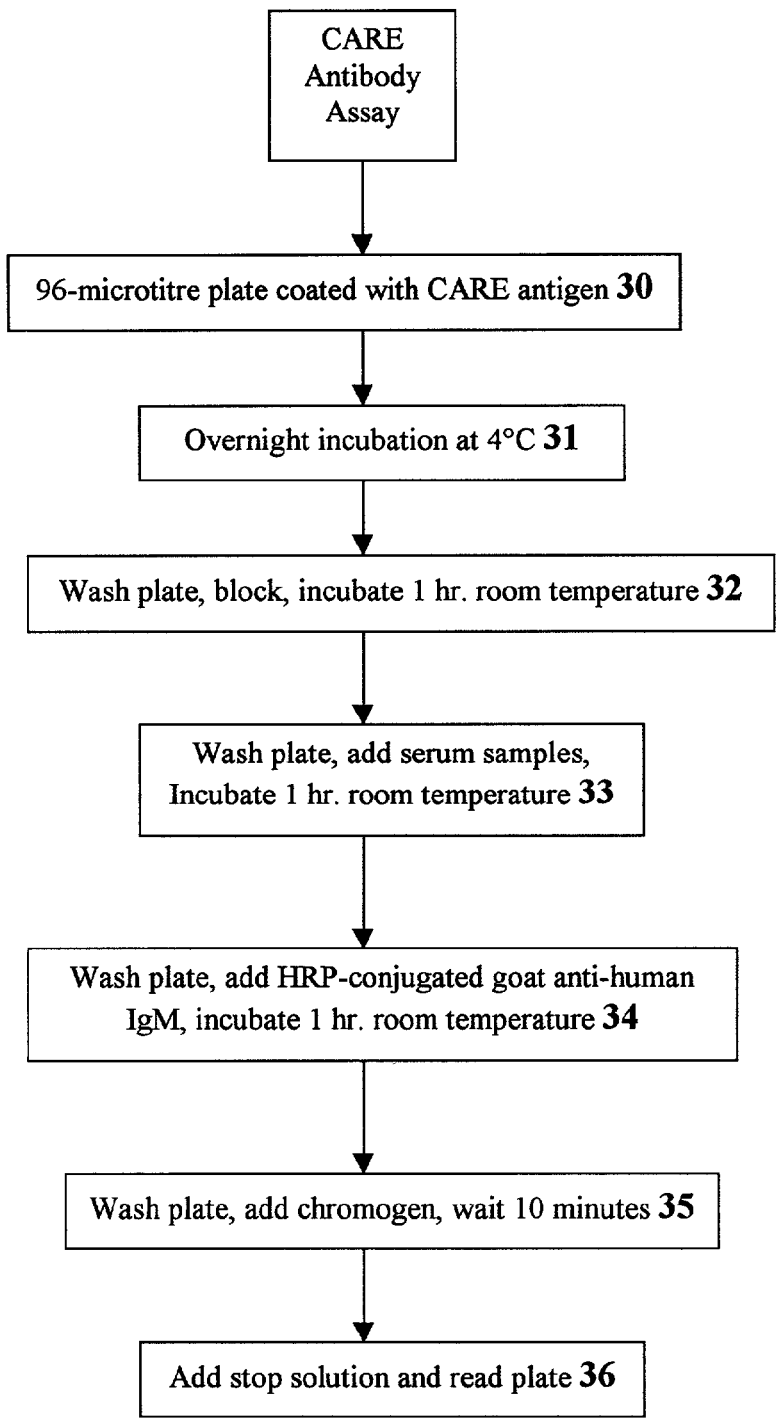
FIG. 4 shows the ELISA assay for the detection of the CARE antigen in serum.

The CARE antibody test is an indirect assay used to detect the presence of the CARE antibody in human serum against the cancer-expressed CARE antigen shown in FIG. 4. Indirect ELISA (enzyme linked immunosorbent assay) surprisingly was extremely effective in detecting and quantifying the CARE antibodies in serum. The wells of a 96-well plate are coated with the CARE antigen that had been obtained as described above (Step 30). The plate is allowed to incubate overnight at 4° C. to facilitate efficient adsorption of the antigen to the plate (Step 31). The plate is washed three times in a 96-well plate washer with plate washing buffer (Step 32). Washing is a necessary and crucial step because it separates bound versus free antigen. After washing, a blocking reagent containing bovine serum albumin is added to prevent nonspecific adsorption of the CARE antibody to the exposed plastic sites where antigen failed to bind. Blocking reagents are immunologically inert and therefore, do not interfere with the subsequent antigen or antibody reactions. After the wells have been blocked, they are allowed to incubate for one hour at room temperature (Step 32). During incubation, serum samples from test patients and reference serum are diluted into buffer. The reference serum or standard is serially diluted by one third concentrations to obtain a standard or calibration curve. After washing, the serum samples and the reference standard are added to the wells. The serum contains the CARE antigen specific antibody, the primary antibody. Upon adding the serum containing CARE antibody to the CARE antigen coated plate, the CARE antibody will bind to the CARE antigen adsorbed to the plate (Step 34). After incubation for one hour at room temperature and subsequent washing, goat anti-human IgM antibody conjugated with horseradish peroxidase (HRP) is added to the wells (Step 34). After washing, chromogen substrate is then added (Step 35), followed by stop solution (Step 36) to determine calorimetrically the product generated by HRP from the chromogen substrate, which provides the mean relative concentration of CARE antibody in the patient serum.

Blood was sampled from healthy volunteers, 130 males and 176 females. The serum mean relative concentration (MRC) was determined for the CARE antibody using the ELISA assay. The mean MRC± the standard deviation (SD) for the CARE antibody for these healthy volunteers was 38.6±41.3 SD. 105 patients with many different types of cancers (breast, melanoma, lymphoma, rectum, CLL, colon, cervical, mylodisplastic, gastric, head and neck, chronic myeloginous leukemia, lung, tonsil) were also studied for the mean relative concentration of antibody in the blood. The MRC for the CARE antibody for these patients with cancer was 352±262 SD. 60 patients with a history of cancer but without any evidence of current cancer were studied and had a mean MRC of 49±60 SD. The ELISA assay of the present invention was able to demonstrate in patients with a broad range of cancers seven times higher serum CARE antibody levels than for normal subjects. In addition, the ELISA test for the CARE antibody also was able to distinguish patients who had cancer but were free of cancer, these patients having a CARE antibody level in the normal range.

3. CARE Antigen ELISA Test.

Figure 5:
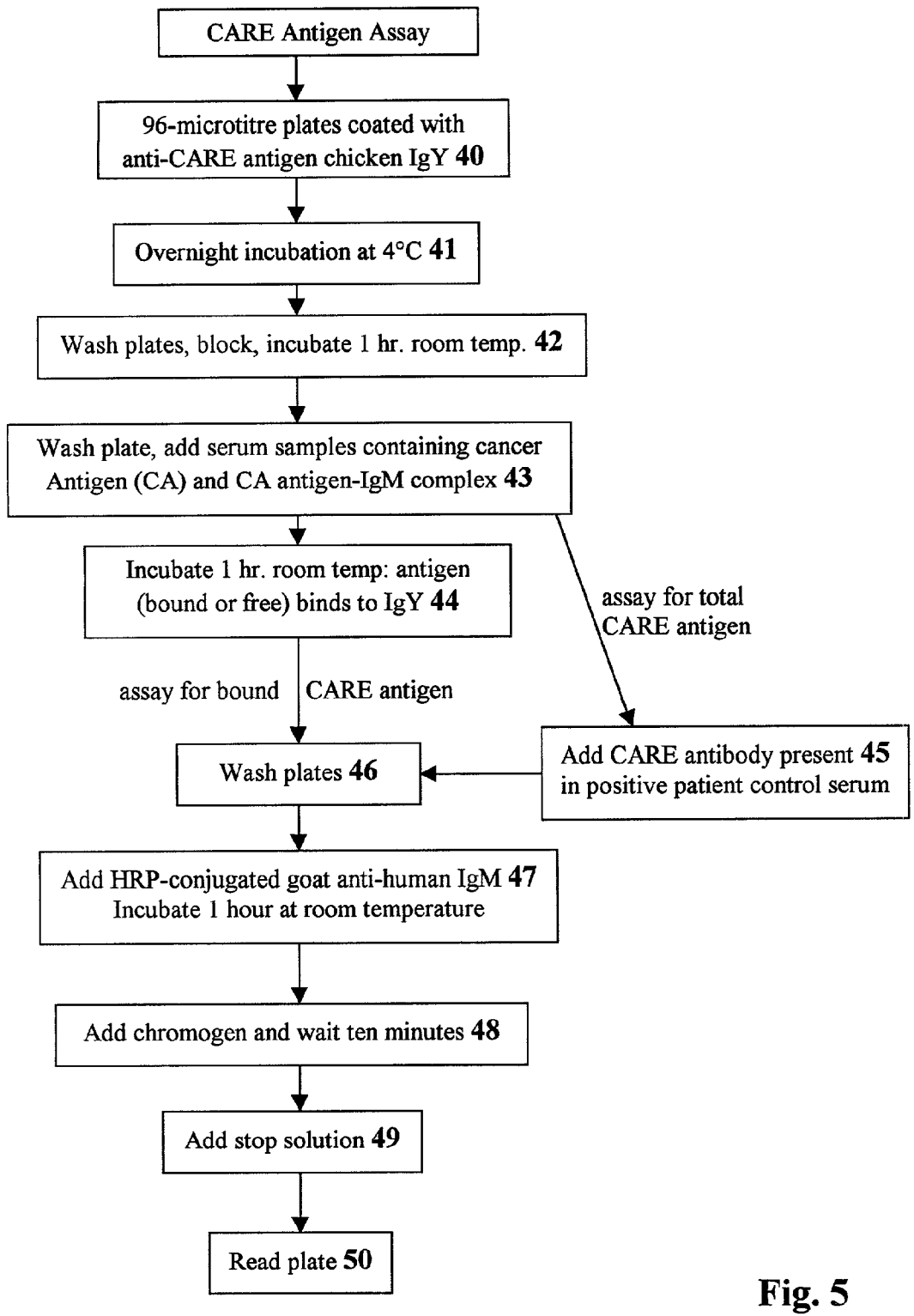
FIG. 5 shows the ELISA assay used to determine the amount of cancer antigen present in serum of patients.

The CARE antigen test is an enzyme-linked immunosorbent assay (ELISA) used to detect the amount of cancer antigen present in serum of patients, shown in FIG. 5. The antigen may be free or bound to the antibody in the form of an immune complex. Total antigen is free plus bound. The CARE antigen test determines the total and bound antigen with the difference being the free antigen. To trap the free and bound antigen from serum, a 96-well microtiter plate is coated overnight with chicken anti-CARE antigen IgY antibody (Step 40). This antibody is derived from the yolk of eggs from chickens innoculated with CARE antigen. The chick antibody adheres to a 96-well plate overnight at 2–4° C. (Step 41). The following day, the plate is washed and coated with a blocking agent and incubated for one hour at room temperature as described previously in the CARE antibody test description (Step 42). After washing, patient sera are added to the plate to incubate for one hour at room temperature. (Step 43). The assay allows both the bound and total antigen to be determined (Step 44). The bound antigen is coated with a solution that will not react with the complex. At the same time, the total antigen is determined in parallel samples where the free antigen is bound by a reference positive patients' CARE antibody against the CARE antigen (Step 45). Standard methods are used to prepare IgM from the pooled serum of cancer patients. IgM (MW 700K) is much larger than any other serum protein component and is purified by size exclusion chromatography. The plate is allowed to incubate for one hour at room temperature after which it is washed (Step 46). Goat anti-human IgM antibody conjugated to horseradish peroxidase (HRP) is added to all the wells. Chromogen is added to all the wells and reacts with the horseradish peroxidase linked to the antibody (Step 48). Stop solution is then added (Step 49). Colormetric readings are made to determine the mean relative concentration of antigen, bound and total, present in the patient's serum (Step 50). The amount of free antigen is obtained by subtracting bound antigen from total antigen.

The ELISA test incorporating the chicken IgY antibody to the CARE antigen was used to measure the CARE antigen in the serum of patients having a large variety of cancers. In this study, the bound antigen and total antigen were measured in 108 healthy volunteers and, in addition, the serum CARE antibody to the CARE antigen was also measured. In the healthy volunteers (n=108), bound antigen was 209 mean relative concentration (MRC)±262 SD and total antigen was 297±328. Antibody was 39±41. The apparent false negative was 5%. In 7 patients diagnosed with a variety of cancers, including breast cancer, lymphoma, myelodysplastic disease, colon cancer, melanoma, lung cancer, rectal cancer, and chronic myelogenous leukemia, the MRC for total CARE antigen was 776±259 and serum CARE antibody was 525±364. Thus, using this assay, patients with various cancers were shown to have 2.6 times higher serum CARE antigen levels than the normal subject and this increased CARE antigen level was associated with an 11 times higher CARE antibody level. Three patients were also studied who were successfully treated for cancer. Two of these patients had breast cancer and one had malignant lymphoma. After treatment for their cancers, these patients had no detectable serum CARE antibody and their serum CARE antigen levels were 124±54. These studies assaying for the serum CARE antibody and serum CARE antigen clearly show the ability of these assays in combination to detect the presence of cancer in a broad range of cancers. They further show the consistency between measuring the antibody and the antigen and strongly indicate the usefulness of combining the tests to get a complete detection of cancer with a high degree of sensitivity and selectivity.

The results of these studies demonstrate that the present invention provides a method and system to increase the diagnostic sensitivity and selectivity not only for cancer but for any disease, compared to existing methods. Application of the present invention by testing both antigen and antibody in fluids or tissues of patients substantially increases the probability of correctly and accurately detecting not only cancer, but any disease, compared to testing only an antigen or only an antibody. The system and method of the present invention will be useful in a variety of cancers, including, for example, leukemia and related blood disorders, lung cancer, breast cancer, colon cancer, prostate cancer, anal cancer, cancer of the bile duct, bladder cancer, bone cancer, bone metastasis, brain and spinal cord cancers, cervical cancer, non-Hodgkin lymphoma, rectal cancer, endometrial cancer, esophageal cancer, gallbladder cancer, gastrointestinal carcinoid tumors, Kaposi's carcinoma, kidney cancer, renal cell carcinoma, laryngeal cancer, hyphopharyngeal cancer, liver cancer, malignant mesothelioma, melanoma, metastatic cancer, multiple myeloma, mylodysplastic syndrome, neuroblastoma, oral cavity cancer, oral pharyngeal cancer, osteosarcoma, ovarian cancer, pancreatic cancer, penile cancer, pituitary cancer, retinblastoma, rhabdomyosarcoma, salivary gland cancer, soft tissue cancer, skin cancer, stomach cancer, testicular cancer, thyroid cancer, uterine cancer, vaginal cancer, vulvar cancer, and Wilm's tumor, and in other diseases, such as, for example, autoimmune disease, heart disease, graft-versus-host disease, and in diseases involving the process of apoptosis.

4. Serum CARE Antibody.

The serum CARE antibody was determined to be an IgM antibody by using a secondary antibody specific for binding to IgM antibodies. As noted above, CARE antigen or CARE antigen fragment can be bound to a microtitre well plate and the CARE IgM antibody can then be bound to the CARE antigen or fragment. The secondary antibody can then be used to detect the CARE IgM antibody. Secondary antibodies against IgG or IgA will not detect the IgM CARE antibody.

Normally, in the primary response to an antigen, there is a sharp increase in serum IgM; however, the concentration of IgM eventually drops as a rise in IgG concentration is seen to increase. This is the process of immunoglobulin class switching or seroconversion. This process is typically irreversible because of deletions of genes within the DNA of memory B cells. This class switch from a high-valency, low affinity immunoglobulin M to a low-valency, high affinity IgG may provide a mechanism for more specific recognition and response upon a second challenge by the antigen. However, the CARE antigen is IgM specific and the CARE IgM antibody reflects no seroconversion to IgG. This is unexpected, and if the CARE IgM antibody were converted to IgG, the CARE antibody test would not be of benefit because IgG is not specific to the CARE antigen. Therefore, it would be impossible to effectively measure CARE antibody concentration specific for the CARE antigen if CARE IgM were converted to IgG. In 13 patients with elevated CARE antibody concentrations, the concentrations of IgG were also measured. The concentration of IgG was only 7.3±4.8% of the CARE antibody concentration.

5. Therapeutic Uses

Both the CARE antigen and the anti-CARE chicken IgY antibodies will have therapeutic utility as vaccines to a large number of cancers. Administration of the CARE antigen will induce an immune response of IgM CARE antibodies which will bind to CARE antigen bound to cancer cells, inducing an immune response to destroy the cancer cells. Also, the anti-CARE chicken IgY antibodies may be administered to a patient and will bind to CARE antigen on cancer cells. The CARE antigen IgY antibody complex will be recognized as foreign and the patient's body will mount an immune response that will destroy the cancer cells. The human IgM CARE antibody, and any one or more types of proteins produced using the CARE antigen, can also be administered directly to patients to bind to CARE antigen and thereby destroy cancer cells. These proteins can be administered individually or in combination.

The foregoing description has been limited to specific embodiments of this invention. It will be apparent, however, that variations and modifications may be made by those skilled in the art to the disclosed embodiments of the invention, with the attainment of some or all of its advantages and without departing from the spirit and scope of the present invention. For example, the polypeptides shown in FIG. 2 may be used in the ELISA antibody assay to substitute for the CARE antigen, and can be used to inoculate chickens to produce the chicken IgY anti-CARE antigen antibody for use in the ELISA CARE antigen assay. They may also be used as vaccines to induce an immune response to the CARE antigen.

It will be understood that various changes in the details, materials, and arrangements of the parts which have been described and illustrated above in order to explain the nature of this invention may be made by those skilled in the art without departing from the principle and scope of the invention as recited in the following claims.

I claim:

1. An ELISA assay for the detection of a CARE antibody, prepared by a process comprising the steps of:
 a) coating a surface with CARE antigen having the amino acid sequence shown in SEQ ID NO: 2;
 b) adding biological samples from a patient;
 c) adding conjugated anti-human IgM antibody; and
 d) detecting anti-human IgM antibody bound to said CARE antigen at SEQ ID NO: 2.

2. The assay according to claim 1 wherein said step of detecting is performed by adding substrate for conjugated anti-human IgM antibody and measuring product produced from said substrate by said conjugated anti-human IgM antibody.

3. The assay according to claim 2 wherein said surface is a microtitre plate, said anti-human IgM antibody is goat anti-human IgM antibody conjugated with horseradish peroxidase, said substrate is chromogen, and said biological samples are sera.

4. A method for detecting cancer comprising the steps of:
 a) isolating and purifying a CARE antigen which has the amino acid sequence of SEQ ID NO:1;
 b) incorporating said antigen into an ELISA assay; and
 c) measuring the level of a human IgM CARE antibody in serum which specifically binds to said antigen at SEQ ID NO:1, wherein an increase in the level of binding relative to the level of binding in normal serum is indicative of cancer.

5. A method for detecting cancer comprising the steps of:
 a) isolating and purifying a CARE antigen which has the amino acid sequence of SEQ ID NO:2;
 b) incorporating said antigen into an ELISA assay; and
 c) measuring the level of a human IgM CARE antibody in serum which specifically binds to said antigen at SEQ ID NO:2, wherein an increase in the level of binding relative to the level of binding in normal serum is indicative of cancer.

6. The method of claim 4 wherein said ELISA assay is prepared comprising the steps of:
 a) coating a surface with said CARE antigen;
 b) adding serum from a patient;
 c) adding conjugated anti-human IgM antibody; and
 d) detecting anti-human IgM antibody bound to said CARE antigen.

7. The method of claim 4 wherein said detecting is produced by adding substrate for conjugated anti-human IgM antibody and measuring product produced from said substrate by said conjugated anti-human IgM antibody.

8. The method of claim 4 wherein said surface is a microtiter plate, said anti-human IgM antibody is goat anti-human IgM antibody conjugated with horseradish peroxidase and said substrate is chromogen.

9. The method of claim 5 wherein said ELISA assay is prepared comprising the steps of:
 a) coating a surface with said CARE antigen;
 b) adding serum from a patient;
 c) adding conjugated anti-human IgM antibody; and
 d) detecting anti-human IgM antibody bound to said CARE antigen.

10. The method of claim 5 wherein said detecting is produced by adding substrate for conjugated anti-human IgM antibody and measuring product produced from said substrate by said conjugated anti-human IgM antibody.

11. The method of claim 5 wherein said surface is a microtiter plate, said anti-human IgM antibody is goat anti-human IgM antibody conjugated with horseradish peroxidase and said substrate is chromogen.

* * * * *

SEQUENCE LISTING

```
<160> NUMBER OF SEQ ID NOS: 2

<210> SEQ ID NO 1
<211> LENGTH: 24
<212> TYPE: PRT
<213> ORGANISM: Human
<220> FEATURE:
<221> NAME/KEY: CHAIN
<222> LOCATION: (1)...(72)
<223> OTHER INFORMATION: No Other Relevant Information on this Sequence

<400> SEQUENCE: 1

Ala Val Val Val Lys Lys Ile Glu Thr Arg Asp Gly Lys Leu Val Ser
                 5                  10                  15

Glu Ser Ser Asp Val Leu Pro Lys
            20

<210> SEQ ID NO 2
<211> LENGTH: 17
<212> TYPE: PRT
<213> ORGANISM: Human

<400> SEQUENCE: 2

Cys Thr Arg Asp Gly Lys Leu Val Ser Glu Ser Ser Asp Val Leu Pro
                 5                  10                  15

Lys
```